United States Patent [19]

Oeda et al.

[11] Patent Number: 4,766,068
[45] Date of Patent: Aug. 23, 1988

[54] CYTOCHROME P-450MC GENE, EXPRESSION PLASMID CARRYING THE SAID GENE, YEASTS TRANSFORMED WITH THE SAID PLASMID AND A PROCESS FOR PRODUCING CYTOCHROME P-450MC BY CULTURING THE SAID TRANSFORMANT YEASTS

[75] Inventors: Kenji Oeda; Toshiyuki Sakaki, both of Toyonaka; Hideo Ohkawa, Takarazuka; Yoshiyasu Yabusaki, Kobe; Hiroko Murakami, Ashiya; Keiko Nakamura, Kobe; Masatoshi Shimizu, Takarazuka, all of Japan

[73] Assignee: Agency of Industrial Science and Technology, Tokyo, Japan

[21] Appl. No.: 741,592

[22] Filed: Jun. 5, 1985

[30] Foreign Application Priority Data

Jun. 16, 1984 [JP] Japan ................................. 59-122953
Aug. 15, 1984 [JP] Japan ................................. 59-169447
Aug. 24, 1984 [JP] Japan ................................. 59-175159

[51] Int. Cl.[4] .................... C12P 21/00; C12P 21/02; C12N 15/00; C07H 15/12
[52] U.S. Cl. ........................................ 435/68; 435/70; 435/172.3; 435/320; 435/255; 435/256; 536/27; 935/37; 935/60; 935/69

[58] Field of Search .................. 435/68, 70, 172–173, 435/255, 256, 317, 320; 536/27; 935/37, 60, 69

[56] References Cited

PUBLICATIONS

Ammerer, *Methods Enzymol* 101: 192–201, 1983.
Murakami, H. et al, *DNA* 5(1): 1–10, 1986.
Oeda, K. et al, *DNA* 4(3): 203–210, 1985.
Yabusaki, Y. et al, *Nucl Acids Res* 12(6): 2929–2938, 1984.
Sakaki, T. et al, *J Biochem* 98: 167–175, 1985.
Yabusaki, Y. et al, *J Biochem* 96: 793–804, 1984.
Kawajiri, K. et al, *J Biochem* 94: 1465–1473, 1983.
Hines, R. N. et al, *Arch Biochem Biophys* 237 (2): 465–476, 1985.

*Primary Examiner*—Thomas G. Wiseman
*Assistant Examiner*—Robin Lyn Teskin
*Attorney, Agent, or Firm*—Ladas & Parry

[57] ABSTRACT

An expression vector, a plasmid containing yeast alcohol dehydrogenase I promoter and terminator and the gene coding for the rat liver cytochrome P-450MC gene *Saccharomyces cerevisiae* transformed with the plasmid and process for preparing rat liver cytochrome P-450MC.

8 Claims, 14 Drawing Sheets

FIG. 1(a)

```
           10        20        30        40        50        60
CATCCTCCCTGGGGTCCTAGAGAACACTCTTCAGTTCAGTCCTTCCTCACAGCCAAAGCA 70        80        90       100       110       120
GCCACCTAGATC[ATG]CCTTCTGTGTATGGATTCCCAGCCTTCACATCAGCCACAGAGCTG
            MetProSerValTyrGlyPheProAlaPheThrSerAlaThrGluLeu 130       140       150       160       170       180
CTCCTGGCCGTCACCACATTCTGCCTTGGATTCTGGGTGGTTAGAGTCACAAGAACCTGG
LeuLeuAlaValThrThrPheCysLeuGlyPheTrpValValArgValThrArgThrTrp 190       200       210       220       230       240
GTTCCCAAAGGTCTGAAGAGTCCACCCGGACCCTGGGGCTTGCCCTTCATAGGGCACGTG
ValProLysGlyLeuLysSerProProGlyProTrpGlyLeuProPheIleGlyHisVal 250       260       270       280       290       300
CTGACCCTGGGGAAGAACCCACACCTGTCACTGACAAAACTGAGTCAGCAGTATGGGGAC
LeuThrLeuGlyLysAsnProHisLeuSerLeuThrLysLeuSerGlnGlnTyrGlyAsp 310       320       330       340       350       360
GTGCTGCAGATCCGTATTGGCTCCACACCCGTGGTGGTGCTGAGCGGCCTGAACACCATC
ValLeuGlnIleArgIleGlySerThrProValValValLeuSerGlyLeuAsnThrIle 370       380       390       400       410       420
AAGCAGGCCCTGGTGAAACAGGGGGATGACTTCAAAGGCCGGCCAGACCTCTACAGCTTC
LysGlnAlaLeuValLysGlnGlyAspAspPheLysGlyArgProAspLeuTyrSerPhe 430       440       450       460       470       480
ACACTTATCGCTAATGGCCAGAGCATGACTTTCAACCCAGACTCTGGACCGCTGTGGGCT
ThrLeuIleAlaAsnGlyGlnSerMetThrPheAsnProAspSerGlyProLeuTrpAla 490       500       510       520       530       540
GCCCGCCGGCGCCTGGCCCAGAATGCGCTGAAGAGTTTCTCCATAGCCTCAGACCCAACA
AlaArgArgArgLeuAlaGlnAsnAlaLeuLysSerPheSerIleAlaSerAspProThr 550       560       570       580       590       600
CTGGCATCCTCTTGCTACTTGGAAGAGCACGTGAGCAAAGAGGCTGAATACTTAATCAGC
LeuAlaSerSerCysTyrLeuGluGluHisValSerLysGluAlaGluTyrLeuIleSer
```

FIG. 1(b)

```
         610       620       630       640       650       660
AAGTTCCAGAAGCTGATGGCAGAGGTTGGCCACTTCGACCCTTTCAAGTATTTGGTGGTG
LysPheGlnLysLeuMetAlaGluValGlyHisPheAspProPheLysTyrLeuValVal 670       680       690       700       710       720
TCAGTGGCCAATGTCATCTGTGCCATATGCTTTGGCAGACGTTATGACCACGATGACCAA
SerValAlaAsnValIleCysAlaIleCysPheGlyArgArgTyrAspHisAspAspGln 730       740       750       760       770       780
GAGCTGCTCAGCATAGTCAATCTAAGCAATGAGTTTGGGGAGGTTACTGGTTCTGGATAC
GluLeuLeuSerIleValAsnLeuSerAsnGluPheGlyGluValThrGlySerGlyTyr 790       800       810       820       830       840
CCAGCTGACTTCATTCCTATCCTCCGTTACCTCCCTAACTCTTCCCTGGATGCCTTCAAG
ProAlaAspPheIleProIleLeuArgTyrLeuProAsnSerSerLeuAspAlaPheLys 850       860       870       880       890       900
GACTTGAATAAGAAGTTCTACAGTTTCATGAAGAAGCTAATCAAAGAGCACTACAGGACA
AspLeuAsnLysLysPheTyrSerPheMetLysLysLeuIleLysGluHisTyrArgThr 910       920       930       940       950       960
TTTGAGAAGGGCCACATCCGGGACATCACAGACAGCCTCATTGAGCATTGTCAGGACAGG
PheGluLysGlyHisIleArgAspIleThrAspSerLeuIleGluHisCysGlnAspArg 970       980       990      1000      1010      1020
AGGCTGGACGAGAATGCCAATGTCCAGCTCTCAGATGATAAGGTCATTACGATTGTTTTT
ArgLeuAspGluAsnAlaAsnValGlnLeuSerAspAspLysValIleThrIleValPhe 1030      1040      1050      1060      1070      1080
GACCTCTTTGGAGCTGGGTTTGACACAATCACAACTGCTATCTCTTGGAGCCTCATGTAC
AspLeuPheGlyAlaGlyPheAspThrIleThrThrAlaIleSerTrpSerLeuMetTyr 1090      1100      1110      1120      1130      1140
CTGGTAACCAACCCTAGGATACAGAGAAAGATCCAGGAGGAGTTAGACACAGTGATTGGC
LeuValThrAsnProArgIleGlnArgLysIleGlnGluGluLeuAspThrValIleGly 1150      1160      1170      1180      1190      1200
AGGGATCGGCAGCCCCGGCTTTCTGACAGACCTCAGCTGCCCTATCTGGAGGCCTTCATC
ArgAspArgGlnProArgLeuSerAspArgProGlnLeuProTyrLeuGluAlaPheIle
```

FIG. 1(c)

```
       1210       1220       1230       1240       1250       1260
CTGGAGACCTTCCGACATTCATCCTTTGTCCCATTCACCATCCCCCACAGCACCATAAGA
LeuGluThrPheArgHisSerSerPheValProPheThrIleProHisSerThrIleArg 1270       1280       1290       1300       1310       1320
GATACAAGTCTGAATGGCTTCTATATCCCCAAGGGACACTGTGTCTTTGTGAACCAGTGG
AspThrSerLeuAsnGlyPheTyrIleProLysGlyHisCysValPheValAsnGlnTrp 1330       1340       1350       1360       1370       1380
CAGGTTAACCATGACCAGGAACTATGGGGTGATCCAAACGAGTTCCGGCCTGAAAGGTTT
GlnValAsnHisAspGlnGluLeuTrpGlyAspProAsnGluPheArgProGluArgPhe 1390       1400       1410       1420       1430       1440
CTTACCTCCAGTGGCACTCTGGACAAACACCTGAGTGAGAAGGTCATTCTCTTTGGTTTG
LeuThrSerSerGlyThrLeuAspLysHisLeuSerGluLysValIleLeuPheGlyLeu 1450       1460       1470       1480       1490       1500
GGCAAGCGAAAGTGCATTGGGGAGACCATTGGCCGACTGGAGGTCTTTCTCTTCCTGGCC
GlyLysArgLysCysIleGlyGluThrIleGlyArgLeuGluValPheLeuPheLeuAla 1510       1520       1530       1540       1550       1560
ATCTTGCTGCAGCAAATGGAATTTAATGTGTCACCAGGCGAGAAGGTGGATATGACTCCT
IleLeuLeuGlnGlnMetGluPheAsnValSerProGlyGluLysValAspMetThrPro 1570       1580       1590       1600       1610       1620
GCCTATGGGCTGACTTTAAAACATGCCCGCTGTGAGCACTTCCAAGTGCAGATGCGGTCT
AlaTyrGlyLeuThrLeuLysHisAlaArgCysGluHisPheGlnValGlnMetArgSer 1630       1640       1650       1660       1670       1680
TCTGGTCCTCAGCATCTCCAGGCTTAGACTGTCCTGGATGCTCACCAGACCAGGTGGCTG
SerGlyProGlnHisLeuGlnAla***

1690       1700       1710       1720       1730       1740
TTCCTAGGATTCAACTTCAGTCAGAAACACAGACCCTGGGGCATTGTGCCTGCCTCCTAC 1750       1760       1770       1780       1790       1800
TTTGGACTTGTTTCTCTATATGCTGAACACAGACACTGGGCACAGCAGAGACCCACAGGA
```

FIG. 1(d)

```
        1810       1820       1830       1840       1850       1860
ACCTCAGATCCTTCTCAAGTTCAGCATCAACTAGGAGACCTAAAAGGGTTATGAGATACC 1870       1880       1890       1900       1910       1920
TGGGCCTCAGAAAACCCCTGAAGAGCTCTCTAGGTCCTCCAGTGGCTGGCTGGTTTGAAA 1930       1940       1950       1960       1970       1980
AATACTTACAACAGGTCATGCCAGGATCTGGCTGGTTACTTTGACAACCGGGAGTAGCCC 1990       2000       2010       2020       2030       2040
AGAATGGAGGGAGAAGAGAACTCAAAATACTGGCACGGAGGTGCTCTTGCCATCTGCTGA 2050       2060       2070       2080       2090       2100
GGCTCAACTGTCTTCCAACATGGGTTTATGACACTACATGTGGGGGTGTAGCACCTTCAT 2110       2120       2130       2140       2150       2160
TTACCCTACATAGA AATAAA CAAGGTCTCCTTGTCCTTGCAAAGCCCATGTTCCTGTTTA 2170       2180       2190       2200       2210       2220
GGAAGGGCTGAGAGTTGTGTGTAGAAAGACCTAAGAACATAGGGACAGACTTTCTGGGCA 2230       2240       2250       2260       2270       2280
GTAAGACCAGGTTTAGAGTAAAGGAATGCCTTTTGAGACAGTATTGTGTAGTCCAGGCTG 2290       2300       2310       2320       2330       2340
CCTCTGAACTTGCTACCAAGGGTGGCCTTGAACTCCTTAATTCTTTTTTCTGCTTTTACC 2350       2360       2370       2380       2390       2400
ACCCTACCAAGTGCTAGGGTACAGTCATGAACCGCTACACCAGCTCTTGGTCTCTTGTCT
```

FIG. 1(e)

```
        2410       2420       2430       2440       2450       2460
TTACTGTATAAAACGTTTCTTTCTTTCTTTTTTTTTAAAGAAAATGTTTGTGCATAAGA 2470       2480       2490       2500       2510       2520
GTTTTTTATTGTGGCCTGTATTTTGCTTATGCATTTGTATTAGTCGTACTTCAATAGATT 2530       2540       2550       2560       2570       2580
TAGATAATTCGCTTAGTGTAATAGAGAAAAATCTAACTCAAGTATCCAGAAATATATAGG 2590       2600       2610       2620       2630       2640
AAAAACGTACCTGAGCTA AATAAA ATATTACCTGGAAAAAAAAAAAAAAAAAAAAAAAA 2650       2660       2670       2680       2690
AAAAAAAAAAAAAAAAAAAAAAAAAAAAAAAAAAAAAAAAAAAAAAAAAAAAAAA
```

Ps: Pst I, Sa: Sau3A I, Ba: Bam H I,
Sm: Sma I, Hd: Hind III, Sl: Sal I,
Pv: Pvu I, St: Stu I, Ec: Eco RI

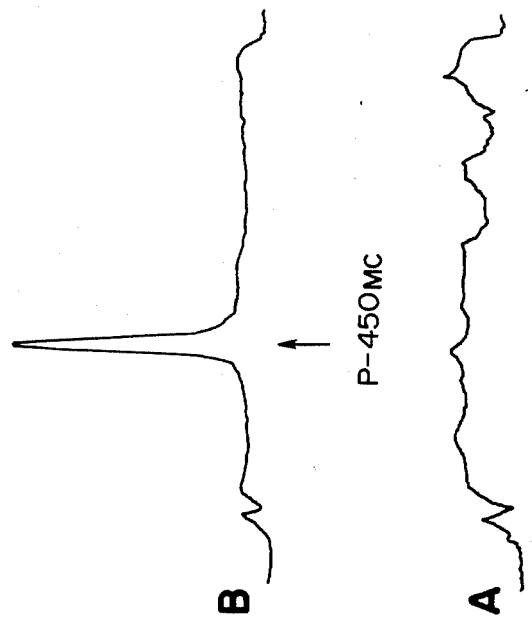
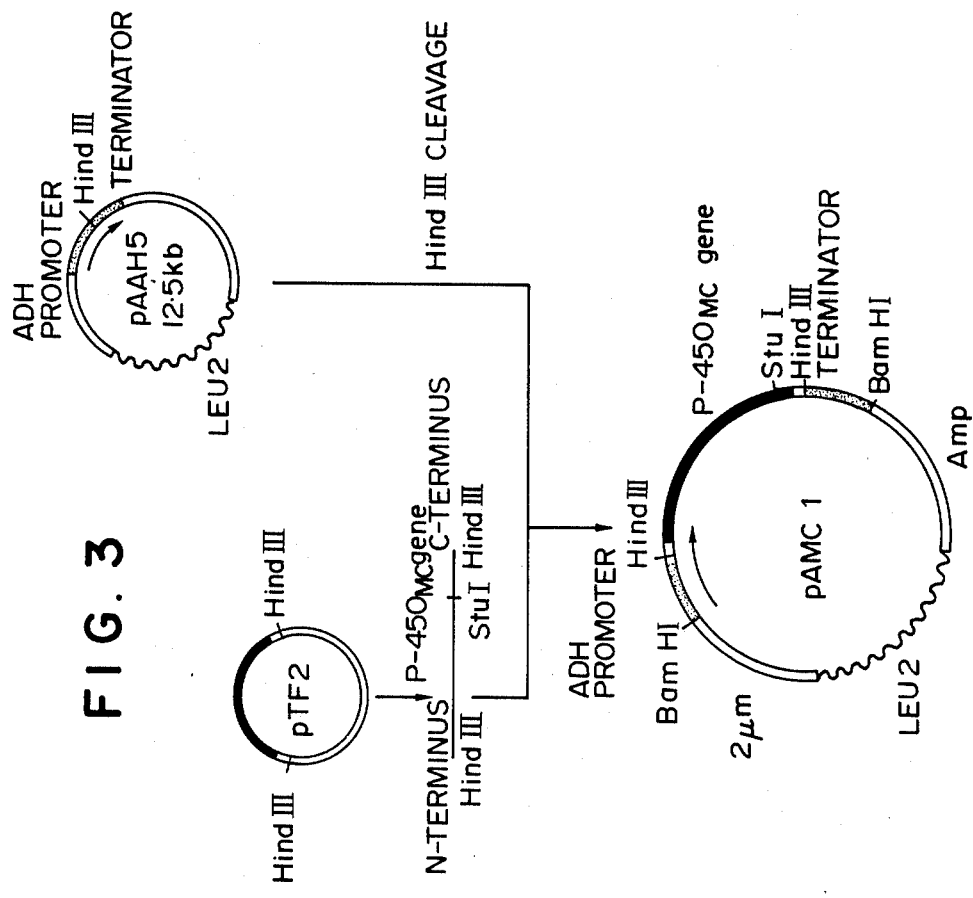

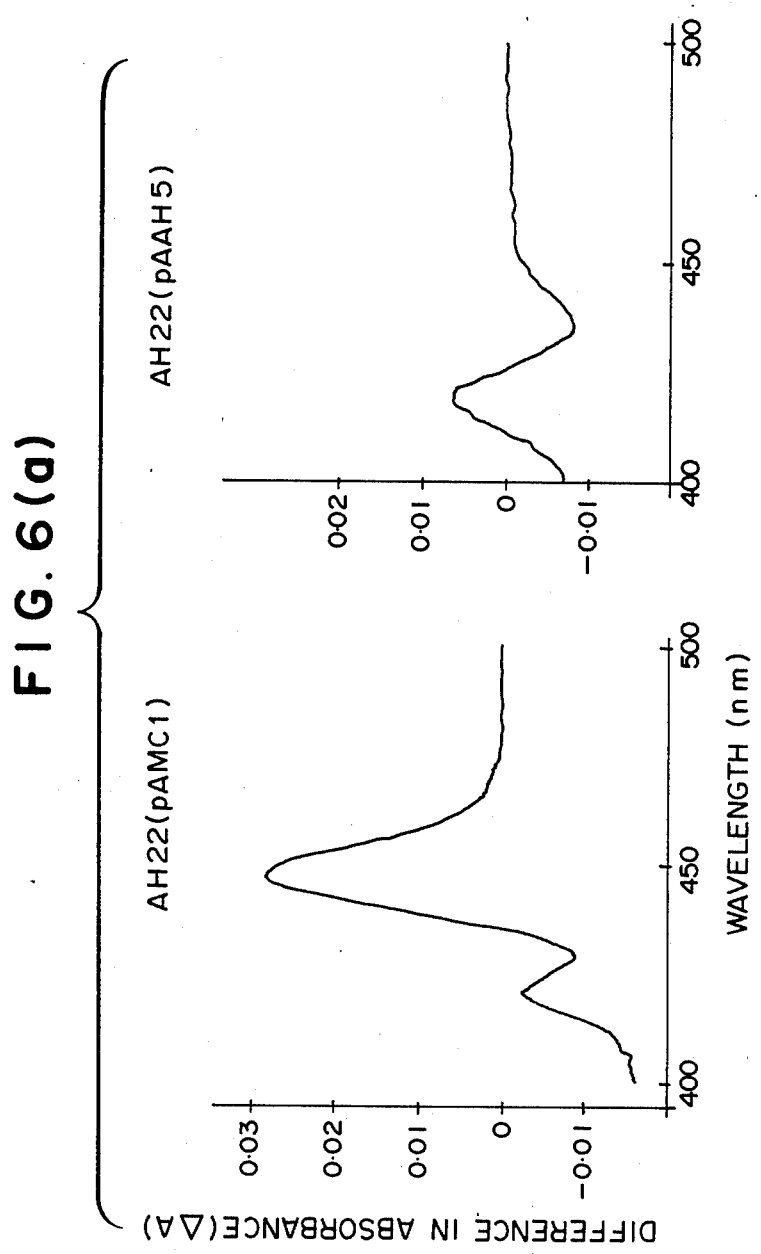

CYTOCHROME P-450MC GENE, EXPRESSION PLASMID CARRYING THE SAID GENE, YEASTS TRANSFORMED WITH THE SAID PLASMID AND A PROCESS FOR PRODUCING CYTOCHROME P-450MC BY CULTURING THE SAID TRANSFORMANT YEASTS

FIELD OF INVENTION

The present invention relates to a genetic engineering technology. More particularly, it pertains to rat liver cytochrome P-450MC gene, plasmids carrying the cytochrome P-450MC gene, transformed yeasts containing the said plasmid which synthesize rat liver cytochrome P-450MC, and to a process for producing rat liver cytochrome P-450MC.

BACKGROUND OF INVENTION

Rat liver cytochrome P-450MC (hereinafter referred to as "P-450MC"), which is inducible by administration of 3-methylcholanthrene (hereinafter referred to as "MC"), is hemoprotein and has a monooxygenase activity towards external aliphatic compounds such as steroids or fatty acids through microsomal electron-transport chains.

Recently, there have been published reports on expression of heterogeneous genes in yeasts by using yeast alcohol dehydrogenase promoter or acidic phosphatase promoter. For example, expressions of a surface antigen of Hepatitis B virus and interferon were reported. Although the number of the reports on expression of heterogeneous genes in yeasts is smaller yet than that of the experiments using E. coli as a host, it is recently increasing.

With respect to P-450MC, whose molecular weight is as large as 59,300 daltons, which contains heme in its molecule and which has a high aryl hydrocarbon hydroxylase activity with a broad substrate spectrum, there has been, however, no report on the expression of its gene in yeasts.

The present inventors have extensively studied on the expression of P-450MC having such characteristics in yeasts, after succeeded in cloning of cDNA coding for P-450MC, constructed a plasmid carrying a ca. 2.7 Kb cDNA insert coding for P-450MC and isolated such plasmids. We reported that P-450MC is a protein consisting of 523 amino acid residues with a molecular weight of 59,300 daltons [Nucleic Acids Research, 12, 2929–2938 (1984)].

Based on these findings, the present inventions have further studied, and now succeeded in constructing a plasmid carrying a DNA fragment coding for P-450MC in such a form that the P-450MC coding region can easily be isolated therefrom as well as in construction of an expression plasmid which expresses the P-450MC gene in yeasts.

Moreover, the present inventors have now prepared transformant yeasts producing P-450MC by transforming yeasts with the said expression plasmids.

The transformant yeasts provided by the present invention produces P-450MC and have a monooxygenase activity which is derived from the P-450MC synthesized in the yeasts.

Thus provided transformant yeast cells, their microsomal fractions, which contain P-450MC, as well as P-450MC per se, which can be isolated therefrom, can be used for oxidation processes or oxidative disposal of organic compounds in industrial wastes.

SUMMARY OF INVENTION

The present invention provides a plasmid wherein a DNA fragment coding for rat liver cytochrome P-450MC is inserted in such a form that the P-450MC coding region can be easily isolated, a process for producing such plasmids, P-450MC gene, a DNA fragment containing the P-450MC gene in such a form that the P-450MC coding region can easily be isolated and a process for producing such DNA fragment. Moreover, the present invention also provides an expression plasmid which expresses the P-450MC gene in yeasts, transformant yeasts which are prepared by transforming yeasts with the said expression vector plasmid and a process for producing P-450MC by culturing the transformant yeasts carrying the plasmids expressing P-450MC.

BRIEF DESCRIPTION OF DRAWINGS

FIGS. 1 (a)–(e) show the nucleotide sequence of rat liver cytochrome P-450MC cDNA cloned in plasmid pAU157 and the amino acid sequence derived therefrom.

FIG. 3 is a diagram of the construction of expression plasmid pAMC1, which enables the P-450MC gene to be expressed in yeasts.

FIG. 5 shows the results of the scanning of P-450MC synthesized in yeasts by a densitometer after electrophoresis. A shows the result of test conducted with Saccharomyces cerevisiae strain SHY3 (pAAH5) which was used as a control. While, B shows the result on S. cerevisiae strain SHY3 (pAMC1).

DETAILED DESCRIPTION OF PREFERRED EMBODIMENTS

Figure 2A:
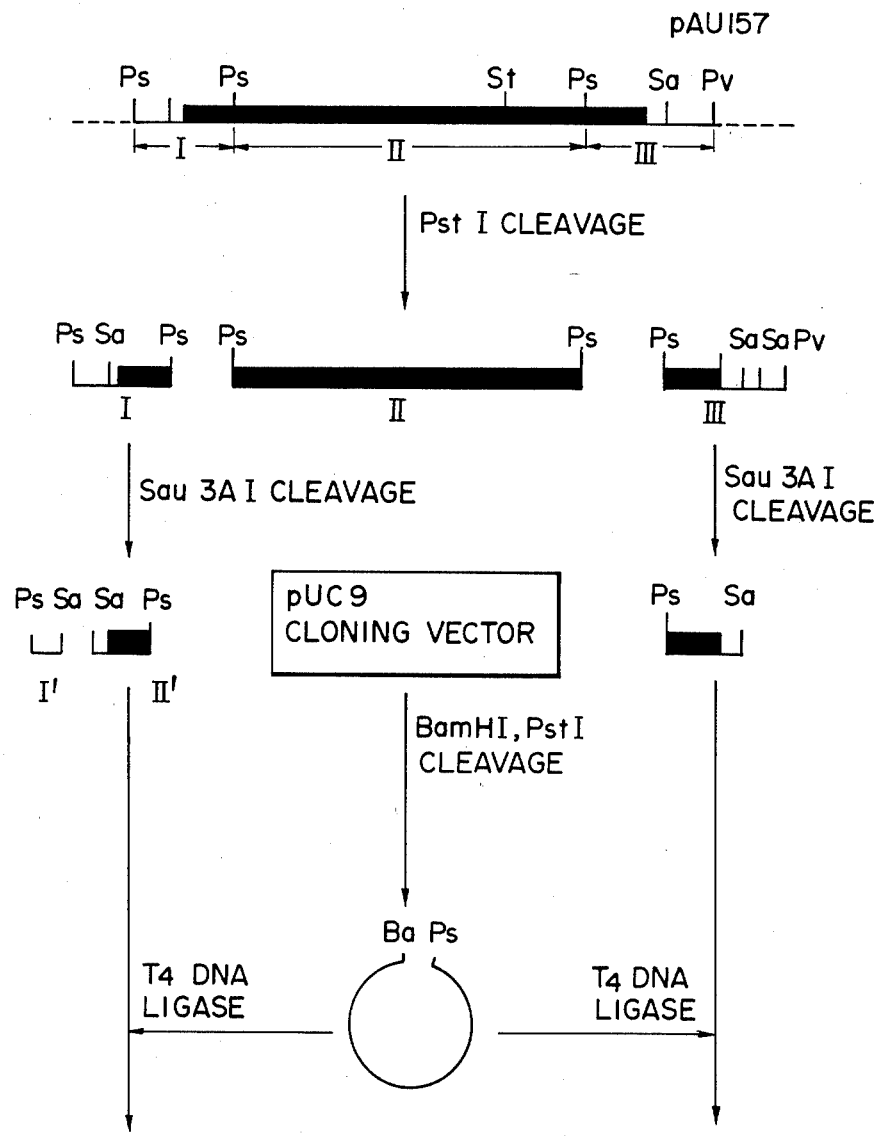
FIGS. 2 (a)–(d) show diagrams of the construction of the plasmid which contains a DNA fragment coding for P-450MC in such a form that the P-450MC coding region can easily be isolated, and of the isolation of the P-450MC coding region therefrom.
Figure 2B:
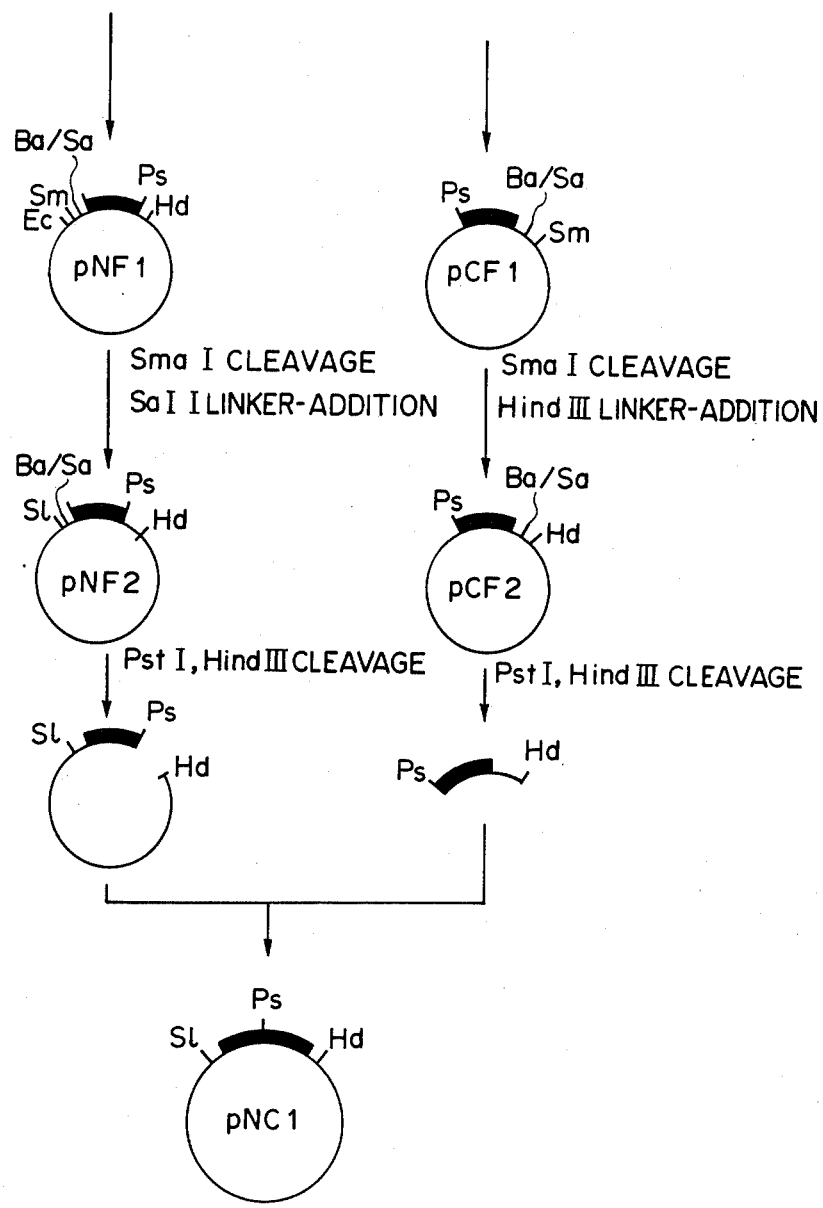
Figure 2C:
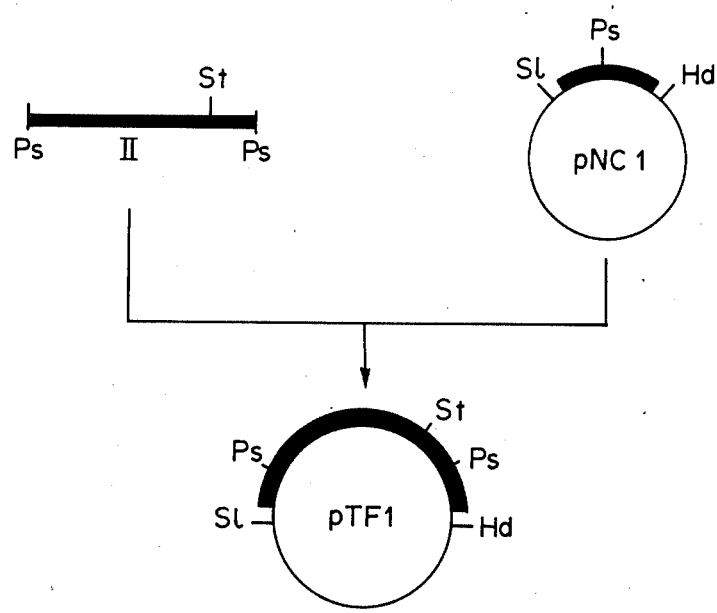
Figure 2D:
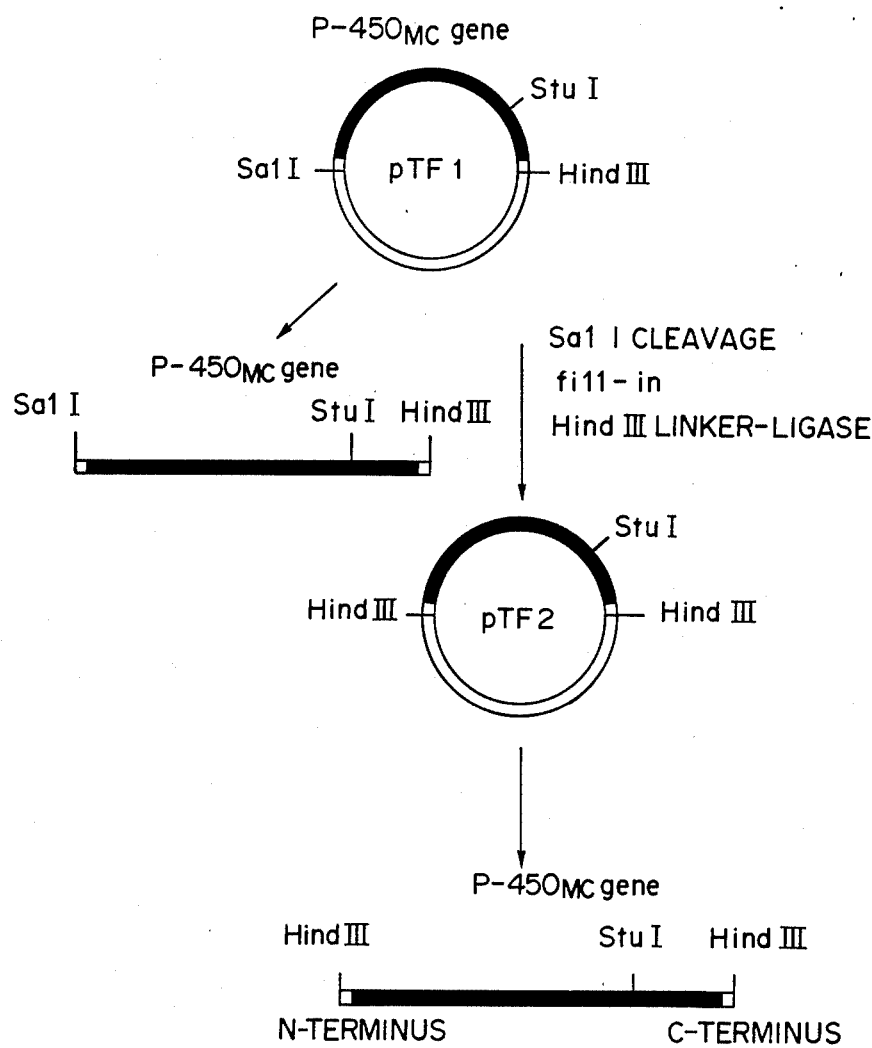

The P-450 MC cDNA fragment of the present invention can be obtained by first isolating the plasmid DNA from E. coli carrying the plasmid pAU157 by a conventional method, and then isolating the P-450 MC coding region, which is the DNA sequence of the nucleotides 73 to 1647 shown in FIG. 1. The isolation of the P-450 MC coding region can be conducted, for example, by the method shown in FIG. 2. That is;

First, plasmid DNA is isolated from E. coli carrying the plasmid pAU157.

Then, a DNA fragment containing the P-450 MC coding region is isolated from the plasmid DNA.

Thirdly, a plasmid, in which a DNA fragment consisting of the P-450MC coding region and restriction endonuclease sites linked to each end of the P-450MC coding region is inserted, is constructed from the DNA fragment.

Finally, the plasmid DNA of thus prepared plasmid is digested with the restriction endonuclease to give the P-450MC gene.

As shown in FIG. 2, the plasmids pTF1 and pTF2 harbor the P-450MC coding sequence to each end of which restriction endonuclease site is linked, and the P-450MC coding region can easily be isolated by cleaving the plasmid DNA at these sites. Further, the restriction sites may be replaced by other suitable restriction sites if desired.

The expression vector plasmid of the present invention may be constructed by inserting the P-450MC coding region obtained as above into an expression vector having an adequate promoter.

For this purpose, there can be used, for example, expression vector plasmid pAAH5 containing yeast alcohol dehydrogenase I (hereinafter referred to as "ADH") promoter and terminator (Washington Research Foundation, Ammerer et al., Methods in Enzymology, 101, part C, p 192–201) ADH promoter is also described in abandoned U.S. Ser. No. 299,733, to Washington Research Foundation.

The expression plasmid of the present invention may be prepared, for example, as shown in FIG. 3.

The recombinant plasmid pAMC1, which is designed for the purpose of expression in yeasts, has an ideal DNA structure as an expression plasmid in that the gene for P-450MC, which shows a high hydroxylase activity, is linked downstream the ADH promoter, which is a potent yeast promoter, and that the transcription stop signal of the ADH gene is located downstream the P-450MC gene.

By introducing the plasmid pAMC1 with such an excellent construction into host yeasts, performing the expression of the P-450MC gene was performed efficiently. A large amount of rat liver cytochrome P-450MC enzyme can be isolated into a purified form.

The transformant yeasts of the present invention can be obtained by transforming yeasts belonging to the genus Saccharomyces, for example, S. cerevisiae strain SHY3 (ATCC 44771), S. cerevisiae strain AH22 (ATCC 38626), S. cerevisiae strain NA87-11A and the like with the expression plasmid of the present invention, for example, the plasmid pAMC1.

The transformation of these yeasts with the plasmid pAMC1 can be performed by, for example, the protoplast method [Nature, 275, 104–109, (1978)].

Cultivation of the Transformants

The transformant yeasts of the present invention can be grown at around 30° C. in a medium containing a carbon source such as glucose or galactose, a nitrogen source containing no amino acid, amino acids which a particular yeast to be grown requires (except leucine) and a base. For example, for growing the transformant yeast, S. cerevisiae strain AH22 (pAMC1), SD-broth [2% dextrose, 0.67% Bacto-yeast nitrogen base w/o amino acids (Difco)] supplemented with 20 μg/ml of histidine is used. As for water to use, distilled water is used and the pH needs not to be adjusted.

In the case where S. cerevisiae strain SHY3 (pAMC1) is to be grown, SD-broth supplemented with 20 μg/ml of histidine, tryptophan and uracil is used.

In the case where S. cerevisiae strain NA87-11A (pAMC1) is grown, the used SD-broth is supplemented with 20 μg of histidine and tryptophan.

Localization of P-450MC synthesized in yeast cells and preparation of the microsomal fraction:

The transformant yeasts of the present invention produce P-450MC in the cells in large quantities, and most of P-450MC is localized in the microsomal fraction in the yeast cells.

Accordingly, the microsomal fraction per se may be used in various oxidation processes such as hydroxylation of benzo(a)pyrene, O-deethylation of 7-ethoxy coumarin and the like, though P-450MC may be isolated and purified from the yeast cells after the cultivation.

The microsomal fraction may readily be prepared by, for example, preparing the protoplasts from the cells, destructing them with ultrasonic wave and centrifuging the resulting mixture.

Isolation and purification of P-450MC

P-450MC can be isolated and purified from the microsomal fraction prepared as above according to the method commonly used for purification of cytochrome P-450. For example, P-450MC can be isolated in a purified form by solubilizing the microsomal fraction with a buffer containing a detergent, and subjecting the solubilized fraction to an adequate combination of column chromatographies using, for example, DEAE-cellulose, hydroxylapatite, DEAE-Sepharose CL-6B, CM-Sephadex and the like. For instance, P-450MC can readily be purified by column chromatography on DEAE-cellulose eluting with potassium phosphate buffer (pH 7.4) containing glycerol, EDTA, etc., whose inorganic electrolyte ( e.g., KCl) concentration is linearly increased in the elution.

The following examples are given to illustrate the present invention more precisely. The present invention is not limited thereto, but usual or obvious modifications or alternations of the disclosed embodiments are possible.

Constructions of P-450MC gene and plasmids containing it

Partial Purification of Cytochrome P-450MC mRNA

3-Methylcholanthrene dissolved in corn oil was intraperitoneally administered to male Sprague-Dawley rats (4 weeks of age, weighing 100–120 g) at a dose of 25 mg/kg of body weight. The rats were sacrificed 14–15 hours after the administration and the livers were removed therefrom. The livers were cut into small pieces and 10 times as much as by volume of 25 mM Tris-HCl (pH 7.5), containing 25 mM NaCl, 5 mM $MgCl_2$, 0.2M sucrose, 5% Triton X-100, and 1 mg/ml of sodium heparine were added thereto. The mixture was then homogenized and centrifuged at $27000 \times g$ for 10 minutes. An equal volume of the same buffer solution containing 20% 2M $MgCl_2$ was added to the resulting supernatant to precipitate polysomes, which were then collected by centrifugation at $26400 \times g$ for 10 minutes and suspended in 5 mM $MgCl_2$ to 50 $A_{260}$/ml. The yield of the polysomes was about 150 $A_{260}$ per g of the liver.

An equal volume of extraction buffer solution (0.2M sodium acetate (pH 5.0), 1% SDS) was added to 20 ml of the polysome suspension. After addition of 40 ml of phenol saturated with the two-fold diluted extraction buffer solution, the mixture was shaken. After the mixture was allowed to stand for a few minutes, 40 ml of chloroform was added to the mixture and shaken again. Thereafter, an aqueous layer and an organic layer were separated by centrifugation at 15000×g for one minute. The aqueous layer was again extracted with 80 ml of chloroform. Extraction with chloroform was repeated until the intermediate layer was no longer formed.

To the aqueous layer thus obtained was added two times as much as by volume of chilled ethanol and allowed to stand at −20° C. overnight to precipitate RNA. After collecting, the RNA was washed twice with 3M sodium acetate (pH 6.0) and dissolved in 0.1M sodium acetate (pH 7.0) followed by precipitation with ethanol. The precipitated RNA was recovered, washed with 75% ethanol, lyophilized and kept at −80° C. The recovery of the RNA from the polysomes was 83–87%.

Thus obtained RNA was subjected to the oligo(dT)-cellulose column chromatography to give a poly(A) mRNA fraction. The RNA was dissolved in a small amount of sterile water, which was in turn diluted with equilibration buffer solution (0.5M NaCl, 10 mM Tris-HCl (pH 7.5), 1 mM EDTA, 0.1% SDS) to 10–15 $A_{260}$/ml. After heated at 65° C. for 5 minutes, the solution was applied to an oligo(dT)-cellulose column previously equilibrated with equilibration buffer solution and the column was washed well with equilibration buffer solution. The fractions eluted with sterile water were collected, to which an aqueous solution of potassium acetate (final concentration of 2%) and chilled ethanol (twice as much as by volume) were added to precipitate the RNA.

Thus obtained RNA was washed with 75% ethanol, dissolved in sterile water and subjected again to the oligo(dT)-collulose column chromatography. With these procedures, approximately 0.12 mg of mRNA was obtained from 1 g of the liver.

The mRNA was then fractioned by centrifugation on a 10–30% sucrose density grandient. The RNA (2–4 $A_{260}$) heated at 65° C. for 5 minutes was laid on a mixture of 0.1M NaCl, 0.5% SDS, 1 mM EDTA and 10 mM Tris-HCl(pH 7.5) with a 10–30% linear sucrose density gradient. After centrifugation at 265000×g for 1 hour with a TV-865 vertical rotor (Du-Pont Sorvall), each 0.3 ml of fraction was collected and mRNA was recovered therefrom by precipitation with ethanol. The mRNA obtained from each fraction was added to a rabbit reticulocyte lysate in vitro translation system in a concentration of 0.3 $A_{260}$/ml and reacted at 30° C. for 1 hour in the presence of 1 mCi/ml of $^{35}$S-methionine as a tracer.

From a part of the reaction mixture was collected a fraction insoluble in TCA, of which radioactivity was measured to determine the total translation activity.

On the other hand, to 25 μl of the reaction mixture, 75 μl of PT buffer solution (0.1M potassium phosphate (pH 7.4), 150 mM NaCl, 2 mM methionine, 2% Triton X-100) was added, followed by 10 μg of anti-P-450 antibody. The mixture was allowed to stand at 4° C. overnight. Protein A-Sepharose CL-4B equilibrated with PT buffer solution (50 μl) was added to the resulting mixture and incubated at 4° C. for 1 hour with stirring at 10 minute intervals. The gel was collected by centrifugation at 12,000 rpm for 5 minutes and washed twice with 1 ml of PT buffer solution. Aquasol (10 ml) was added to the gel and the radioactivity absorbed on the gel was measured. This activity was used as the P-450MC synthesizing activity.

The total translation activity had a peak at 18–20S fraction and the P-450MC synthesizing activity had a peak at around 18S. In the fraction having the highest P-450MC synthesizing activity, approximately 4.7% of the total mRNA was P-450MC mRNA. In view of this, cDNA synthesis was conducted using three fractions (16–23S), i.e. the fraction with the highest P-450MC synthesizing activity and its two neighboring fractions.

cDNA cloning cDNA cloning was conducted according to the Okayama-Berg method. First, a primer DNA and a linker DNA were prepared from plasmids pSV 7186 (P-L Biochemicals) and pSV 1932 (P-L Biochemicals). Approximately 60 dTs and 5–10 dGs were added to the primer and the linker, respectively, using terminal transferase. Thus prepared primer (1.4 μg) and about 2 μg of the mRNA, which was previously heated at 65° C. for 5 minutes, were added to a mixture of 50 mM Tris-HCl (pH 8.3), 8 mM $MgCl_2$, 30 mM KCl, 0.3 mM DTT and 2 mM dNTPs. After 5.5 units of reverse transcriptase was added, the mixture was incubated at 45° C. for 20 minutes. After treating with phenol-chloroform, DNA was recovered from the mixture by precipitation with ethanol. Thus obtained DNA was then subjected to dC-addition with terminal transferase and the addition of 10–20 dCs was confirmed. The product was recovered by precipitating with ethanol and digested with Hind III.

In 10 μl of 10 mM Tris-HCl (pH 7.5) containing 1 mM EDTA and 0.1M NaCl, a mixture of 0.02 pmol of the DNA obtained as above and 0.04 pmol of the linker DNA was incubated at 65° C. for 2 minutes and at 42° C. for 30 minutes and cooled to 0° C. To the mixture, 20 mM Tris-HCl (pH 7.5), 4 mM $MgCl_2$, 10 mM $(NH_4)_2SO_4$, 0.1M KCl, 0.1 mM β-NAD, 50 μg/ml BSA and 10 units of DNA ligase were added and the total volume of the mixture was made up to 100 μl.

After incubated at 12° C. overnight, 40μM dNTPs, 0.15 mM β-NAD, 2 units of DNA ligase, 5 units of DNA polymerase I and 1.25 units of ribonuclease H were added to the mixture and the total volume of the mixture was made up to 104 μl.

The mixture was incubated at 12° C. for 1 hour and then at 25° C. for 1 hour. By using thus obtained DNA solution, *Escherichia coli* strain DH1 was transformed and ampicillin-resistant colonies were selected.

Selection of P-450MC cDNA Clone

In order to select the clones containing P-450MC cDNA from the ampicillin-resistant colonies obtained as above, positive hybridization translation assay and immunoprecipitation assay were performed. The *E. coli* carrying the plasmid was cultured. After the plasmid DNA was amplified by addition of chloramphenicol, the plasmid DNA was prepared according to the method of Birnboim-Doly. The plasmid DNA (20 μg) was linearized by digesting with BamHI, boiled for 10 minutes and rapidly cooled. Subsequently, an equal volume of 1N NaOH was added to the mixture and the mixture was allowed to stand at room temperature for 20 minutes. The mixture was neutralized by addition of ½ volume of a neutralizing buffer solution (1N NaCl, 0.3M sodium citrate, 0.5M Tris-HCl (pH 8.0), 1N HCl) and cooled on ice.

This denatured DNA was applied to 3 mm$^2$ nitrocellulose filter, which was then air-dried and washed twice with 6×SSC (50 ml). After air-dried, the filter was heated at 80° C. for 2 hours.

Sterile water (1 ml) was added to the filter, which was then boiled for one minute and washed with 1 ml sterile water. To this filter were added 80 μl of a hybridization solution [100–500 μg/ml poly(A) RNA, 65% deionized formamide, 20 mM PIPES (pH 6.4), 0.2% SDS, 0.4M NaCl, 100 μg/ml tRNA] which was warmed to 70° C. and the mixture was incubated at 50° C. for 3 hours. The filter was washed ten times with 1 ml of 10 mM Tris-HCl (pH 7.6) containing 0.15M NaCl, 1 mM EDTA and 0.5% SDS, while keeping the mixture to 65° C. The filter was washed twice with the same buffer, which contains, however, no SDS. The filter was added to 300 μl of sterile water containing 30 μg of tRNA, boiled for 1 minute and rapidly cooled in dry ice-ethanol. The precipitated mRNA was treated with phenol-chloroform and recovered by precipitation with ethanol.

The mRNA was washed twice with 70% ethanol and dissolved in 5 μl of sterile water, which was then added to the in vitro translation system to perform the protein synthesis according to the aforementioned method.

The immunoprecipitate of the resulting protein and anti-P-450MC antibody were analyzed by SDS-polyacrylamide gel electrophoresis.

Those clones which hybridized with the mRNA and gave an in vitro translation product whose mobility was the same as that of p-450MC were judged positive. Among the five positive clones, one clone was named as pAU157.

Restriction mapping of pAU157 cDNA insert

For the determination of the restriction map of pAU157 cDNA insert, the plasmid DNA was prepared first and digested with various restriction endonucleases.

The sizes of the resulting DNA fragments were analyzed on 0.8–1.1% agarose gel electrophoresis as well as 5% polyacrylamide gel electrophoresis.

Figure 4:
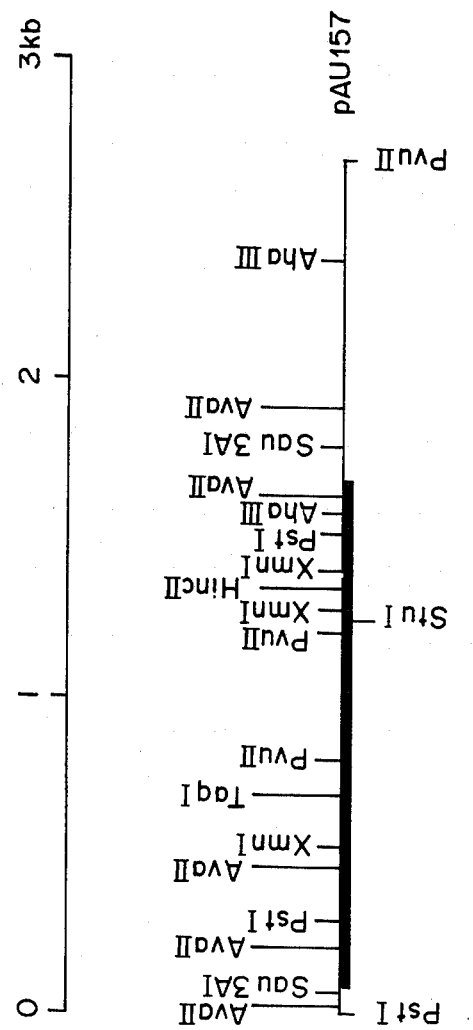
FIG. 4 shows the restriction map of cDNA insert of the plasmid pAU157. The bold line in this FIG. 4 indicates the P-450MC coding region.

The restriction map shown in FIG. 4 was determined by the analysis of the cleavage patterns of the plasmid DNA with a variety of restriction enzymes. This map was completely different from those of the previously reported P-450 cDNA clones prepared from the MC-administered rat liver. Those enzymes which have no recognition site on the pAU-157 cDNA insert were Acc I, Ava I, Bam HI, Bgl II, Eco RI, Hind III, Nar I, Sph I and Stu I.

Determination of nucleotide sequence of pAU157 cDNA

The nucleotide sequence of the entire pAU157 cDNA insert was determined according to the Maxam-Gilbert method.

The plasmid DNA was digested with restriction enzymes. 5'-Terminal phosphate groups of the resulting DNA fragments were removed and the 5'-termini of the DNA fragments were labeled with $^{32}$P by using polynucleotide kinase and γ-$^{32}$P-ATP. The labeled fragments were digested with other restriction enzymes and subjected to the base-specific chemical modification and cleavage.

The resulting fragments were analyzed on denatured polyacrylamide gel electrophoresis. The nucleotide base sequence was determined by autoradiography. The complete nucleotide sequence of the pAU157 cDNA insert is given in FIG. 1.

In the FIG. 1, the first C subsequent to the dG-homopolymer linking the insert to the vector DNA was given the nucleotide number 1. At nucleotide No. 73, there is A of the translation start codon ATG and at nucleotide No. 1645–1647 the stop codon TAG. Accordingly, the sequence of nucleotides 73–1644 was considered to be the reading frame coding for the protein.

There are two other possible interpretations of the reading frame differing from the aforesaid one by + or −1 nucleotide, but they can not encode P-450MC, which was thitherto considered to have a molecular weight of 56,000. It was found that the nucleotide sequence of the longest reading frame corresponds to 524 amino acids. The amino acid sequence of P-450MC is given in FIG. 1. The sequence of 22 amino acid residues from the second to the twenty third amino acids of the P-450MC shown in FIG. 1 was found to completely agree with the amino acid sequence determined with purified P-450MC. From this, we could conclude that the cDNA clone obtained as above corresponds to P-450MC mRNA.

The fact that the first amino acid residue of the purified enzyme was proline suggested that the methionine coded by the translation initiation codon ATG was removed after the translation.

The molecular weight of P-450MC was found to be 59,300 when culculated with the 523 amino acids of P-450MC ignoring the methionine.

On the other hand, with respect to the noncoding region, it was found from the results of some other experiments that a sequence of 30 bp was lacking at the 5'-terminal region. At the 3'-terminal region, sequences of AATAAA, which are considered to be addition signals of poly(A) chain of eucaryotic mRNA, were found at both nucleotides 2115 and 2599, and that 61–62 bp of poly(A) sequence existed at the 3'-terminal.

Accordingly, it was made clear that the pAU157 cDNA insert contains nearly the full length of the coding sequence of P-450MC mRNA.

Preparation of a DNA fragment corresponding to the P-450MC coding region and restriction sites located at each end of the P-450MC coding region and a plasmid carrying the same As the outline is shown in FIG. 2, the P-450MC gene was isolated from the plasmid pAU157 as a DNA fragment corresponding to the P-450MC coding region and two restriction sites attached to each end of the P-450MC coding region and a plasmid containing such DNA fragment was constructed.

These constructions are more precisely illustrated in the following examples:

Step 1: Construction of recombinant plasmid pNF2

(a): A mixture of 10 μg of pAU157 plasmid DNA and 10 units of Pst I (Takara Shuzo, Japan) was incubated at 37° C. for 1 hour in 50 μl of Pst I reaction mixture (20 mM Tris-HCl (pH 7.5), 10 mM MgCl$_2$, 50 mM (NH$_4$)$_2$SO$_4$, 0.01% bovine serum albumin). The reaction mixture was then electrophoresed on 0.8% low melting point agarose gel (Bethesda Research Laboratories) containing 0.1 μg/ml of ethidium bromide (Aldorich) at 100V for 90 minutes. The gel band corresponding to the DNA fragment I (ca. 330 bp. see FIG. 2) was isolated under ultraviolet light and the isolated gel was heated at 65° C. for 5 minutes in an Eppendorf tube. To the molten gel was added 2 volumes of TE buffer [10 mM Tris-HCl (pH 8.0), 0.5 mM EDTA]. The mixture was subjected to extraction with an equal volume of phenol saturated with TE-buffer and centrifuged at 10,000 rpm for 5 minutes. The upper layer was isolated and 2 volumes of chilled ethanol was added thereto. The mixture was allowed to stand at −80° C. for 10 minutes to precipitate DNA.

Thereafter, approximately 1 μg of the DNA fragment I was recovered by centrifugation at 10,000 rpm for 10 minutes, which was then suspended in 20 μl of distilled water.

(b): Thus prepared DNA fragment I (1 μg) and 1 unit of Sau 3AI (Takara Shuzo) were incubated at 37° C. for 1 hour in 50 μl of Sau 3AI reaction mixture [10 mM Tris-HCl (pH 7.5), 7 mM $MgCl_2$, 100 mM NaCl], and DNA was then recovered by extraction with phenol followed by precipitation with ethanol in the same way as above. The recovered DNA was a mixture of DNA fragments I′ and II′ as shown in FIG. 2.

(c): A mixture of 2 μg of pUC 9 cloning vector (P-L Biochemicals), 2 units of Bam HI (Takara Shuzo) and 2 units of Pst I was incubated at 37° C. for 1 hour in 50 μl of Bam HI reaction mixture [10 mM Tris-HCl (pH 8.0), 7 mM $MgCl_2$, 100 mM NaCl, 2 mM 2-mercaptoethanol, 0.01% bovine serum albumin]. DNA was recovered by extraction with phenol followed by precipitation with ethanol. The recovered DNA was suspended in 20 μl of distilled water.

(d): The DNA fragments obtained in the steps (b) and (c) as above, 20 μl each were combined and incubated at 16° C. for 3 hours with 5 units of $T_4$ DNA ligase (Takara Shuzo) in 60 μl of $T_4$ DNA ligase reaction mixture [66 mM Tris-HCl (pH 7.6), 6.6 mM $MgCl_2$, 10 mM dithiothreitol, 10 mM ATP]. Then, E coli strain JM 103 [Δ(lac-pro), thi, str A, sup E, end A, sbc B, hsd R−, F′tra D 36, pro AB, lac I$^q$, Z Δ45; P-L Biochemicals] was transformed with the resulting reaction mixture according to the method of Cohen et al [Proc. Natl. Acad. Sci., U.S.A., 69, 2110–2114 (1972)].

For growing the E. coli JM 103, LB-broth (10 g of polypeptone, 5 g of yeast extract and 5 g of NaCl per 1 l) was used and, as a LB-plate, LB-broth to which 12 g of agar per 1 l of LB-broth was added was used. The same medium and plate were used in the subsequent examples.

In order to clone the desired DNA fragment I″, the transformants were spread on LB-plates which contained 200 μg/l of 5-bromo-4-chloro-3-indolyl-β-D-galactoside (Nakarai Chemical), 2 μmole/ml iso propylthiogalactoside (Tokyo Kasei) and 25 μg/ml of ampicillin (Sigma Co.) and white colonies appearing in blue colonies were isolated according to the method of Rüther et al [Mol. Gen. Genetics, 178, 475–477 (1980)].

In accordance with the procedures of Birnboim et al. [Nucl. Acids. Res. 7, 1513–1523 (1979)], plasmid DNA was isolated from the white colonies.

To thus obtained plasmid DNA (1 μg), restriction endonuclease Eco RI (1 unit) and Pst I (1 unit) were added and the mixture was incubated at 37° C. for 1 hour in Pst I reaction mixture. Recombinant plasmids containing the desired DNA fragment I″ were selected by the 0.8% agarose gel electrophoresis analysis. Thus obtained plasmid was named as pNF1.

(e): According to the above mentioned procedures of Birnboim et al., 5 μg of pNF1 DNA was prepared and digested with 5 units of restriction endonuclease Sma I at 37° C. for 1 hour in 50 μl of Sma I reaction mixture [10 mM Tris-HCl (pH 8.0), 7 mM $MgCl_2$, 20 mM KCl, 7 mM 2-mercaptoethanol, 0.01% bovine serum albumin]. DNA was recovered from the reaction mixture and suspended in 20 μl of distilled water. Then, 2 μg of Sal I linker (Takara Shuzo) and 10 units of $T_4$ DNA ligase were added to about 2 μg of the resulting DNA solution and the mixture was incubated at 16° C. for 3 hours in 60 μl of $T_4$ DNA ligase reaction mixture. With the resulting reaction mixture, E. coli DH1 (F−, rec A1, end A1, gyr A96, thi-1, hsd R17, Sup E 44, λ−) was transformed and spread onto LB plates containing 25 μg/ml of ampicillin. From the resulted colonies, plasmid DNA was isolated. One unit of restriction endonuclease Sal I (Takara Shuzo) was added to 1 μg of the plasmid DNA and the mixture was incubated at 37° C. for 1 hour in 50 μl of a reaction mixture [10 mM Tris-HCl (pH 7.5), 7 mM $MgCl_2$, 175 mM NaCl, 0.2 mM EDTA, 7 mM 2-mercaptoethanol]. By analyzing on 0.8% agarase gel electrophoresis, a plasmid with the Sal I cleavage site was selected, which was named as pNF 2.

Step 2: Construction of recombinant plasmid pCF2

(a): A mixture of 10 μg of plasmid pAU-157 DNA, 10 units of restriction enzyme Pst I and 10 units of restriction enzyme Pvu II (Takara Shuzo) was incubated at 37° C. for 1 hour in 50 μl of a reaction mixture [20 mM Tris-HCl (pH 7.5), 10 mM $MgCl_2$, 50 mM $(NH_4)_2SO_4$, 0.01% bovine serum albumin]. The reaction mixture was analyzed by 0.8% low melting point agarose gel electrophoresis and an approximately 1200 bp of Pvu II-Pst I fragment located at the 3′-terminal of the P-450MC cDNA was isolated in the same way as mentioned above.

(b): A mixture of about 1 μg of the Pvu II-Pst I fragment obtained as above and 1 unit of restriction enzyme Sau 3AI was incubated at 37° C. for 1 hour in 50 μl of Sau 3AI reaction mixture and DNA was recovered and suspended in 20 μl of distilled water.

(c): With the same procedures as of Step 1: (c), the cloning vector pUC 9 was cleaved with restriction endonucleases Bam HI and Pst I.

(d): Each 20 μl of the DNA fragments prepared in (b) and (c) were combined and 5 units of $T_4$ DNA ligase was added to the mixture, which was then incubated at 16° C. for 3 hours.

Thereafter, E. coli strain JM 103 was transformed with the reaction mixture in the same way as that of step 1 (d) and white colonies were selected.

Plasmid DNA was isolated from the white colonies To 1 μg of thus obtained plasmid DNA were added 1 unit of restriction enzyme Pst I and 1 unit of Sma I and the mixture was incubated at 37° C. for 1 hour.

Plasmids containing the DNA fragment III′ were selected by 0.8% agarose gel electrophoresis analysis and named as pCF 1.

(e): According to the above method of Birnboim et al, 5 μg of plasmid pCF1 DNA was prepared, to which 5 units of restriction enzyme Sma I was then added. The mixture was incubated at 37° C. for 1 hour in 50 μl of Sma I reaction mixture. DNA was recovered from the reaction mixture and suspended in 20 μl of distilled water. To about 2 μg of this DNA solution were added 2 μg of Hind III linker (Takara Shuzo) and 10 units of $T_4$ DNA ligase and the mixture was incubated at 16° C. for 3 hours in 60 μl of $T_4$ DNA ligase reaction mixture. Then, E. coli DH1 was transformed with the reaction mixture in the same manner as mentioned above and plasmid DNA was isolated from the resulted colonies.

To 1 μg of the plasmid DNA was added 1 unit of restriction enzyme Sal I and the mixture was incubated in 50 μl of Hind III reaction mixture [10 mM Tris-HCl (pH 7.5), 7 mM MgCl$_2$, 60 mM NaCl] at 37° C. for 1 hour and analyzed by 0.8% agarose gel electrophoresis to give plasmids with the Hind III cleavage site, which was named as pCF2.

Step 3: Construction of recombinant plasmid pNCl (a): To 5 μg of plasmid pNF2 DNA were added 5 units of restriction enzyme Pst I and 5 units of Hind III. The mixture was incubated at 37° C. for 1 hour in 50 μl of Hind III reaction liquid. Thereafter, DNA was recovered from reaction mixture and suspended in 20 μl of distilled water.

(b): Using 5 μg of plasmid pCF2 DNA, the same procedures as above were repeated to give DNA, which was then subjected to 0.8% low melting point agarose gel electrophoresis. The fraction containing a smaller Pst I-Hind III DNA fragment was taken out, which was then subjected to phenol extraction and ethanol precipitation to recover DNA fragment. The DNA fragment was suspended in 20 μl of distilled water.

(c): The DNA solutions obtained with the above procedures (a) and (b) (20 μl each) were combined, to which 5 units of T$_4$ DNA ligase was added. The mixture was incubated at 16° C. for 3 hours in 60 μl of T$_4$ DNA ligase reaction mixture. With the resulting reaction mixture was transformed *E. coli* DH1 by a conventional mehtod. From the resulting colonies, plasmid DNA was isolated. After 1 unit of restriction enzyme Sal I and 1 unit of restriction enzyme Hind III were added to 1 μg of thus obtained plasmid DNA, the mixture was incubated at 37° C. for 1 hour in 50 μl of Hind III reaction mixture. Plasmids containing the desired DNA construction were selected by analyzing by 0.8% agarose gel electrophoresis and named as pNC1.

Step 4: Construction of recombinant plasmic pTF1

(a): To 1 μg of pNC1 DNA was added 1 unit of restriction enzyme Pst I. The mixture was then incubated at 37° C. for 1 hour in 50 μl of Pst I reaction mixture. After DNA was recovered from the reaction mixture, it was suspended in 20 μl of distilled water. To this DNA solution, 1.5 units of alkaline phosphatase (Takara Shuzo) was added and the mixture was incubated at 60° C. for 1 hour in 100 μl of an alkaline phosphatase reaction mixture [50 mM Tris-HCl (pH 8.0)]. After the reaction was over, phenol extraction was performed twice and DNA was precipitated with ethanol, collected and suspended in 20 μl of distilled water.

(b): To 10 μg of pAU157 plasmid DNA was added 10 units of restriction enzyme Pst I and the mixture was incubated at 37° C. for 1 hour in 50 μl of Pst I reaction mixture. DNA was recovered from the reaction mixture, which was then subjected to 0.8% agarose gel electrophoresis. A part of the gel where the desired DNA fragment II was contained was taken out and the DNA was recovered from it and suspended in 20 μl of distilled water.

(c): The DNA solutions obtained with the above procedures (a) and (b) (20 μl each) were combined and 5 units of T$_4$ DNA ligase was added to the mixture, which was then incubated at 16° C. for 3 hours in 60 μl of T$_4$ DNA ligase reaction mixture. With the resulting reaction mixture was transformed *E. coli* DH1.

(d): Plasmid DNA was isolated from the resultant colonies. To 1 μg of the plasmid DNA were added 1 unit of restriction enzyme Sal I and 1 unit of restriction enzyme Hind III and the mixture was incubated at 37° C. for 1 hour in 50μl of Hind III reaction mixture. Electrophoresis analysis on 0.8% agarose gel was performed to provide plasmids containing an about 1.8 kb DNA fragment.

Since the DNA fragment II may be inserted in the plasmid in an opposite direction, the plasmid was further analyzed. To 1 μg of the plasmid obtained as above were added 1 unit of restriction enzyme Hind III and 1 unit of restriction enzyme Stu I (Nippon Gene) and the mixture was incubated at 37° C. for 1 hour in 50 μl of Stu I reaction mixture [10 mM Tris-HCl (pH 7.5), 100 mM NaCl, 10 mM MgCl$_2$, 6 mM 2-mercaptoethanol, 0.1 mg/ml bovine serum albumin]. Electrophoresis analysis on 0.8% agarose gel was performed to select a plasmid containing the DNA fragments I″, II and III′ in the orientation of I″→II→III′. The selected plasmid was named as pTF 1.

By cleavage with Sal I and Hind III, a DNA fragment containing the P-450MC coding region can be isolated from the pTF 1. The restriction endonuclease sites attached to each end of this DNA fragment can readily be converted to other kinds of restriction sites by a conventional method, for example, converting the both ends of the fragment into their blunt forms by modifying with DNA polymerase I or digesting with S1 nuclease and then adding linkers with a desired restriction site to the termini.

Examples of conversion of the terminal restriction sites of the P-450MC fragment and of isolation of the P-450MC coding region are given below:

Conversion of the terminal restriction sites

A mixture of 1 μg of plasmid pTF1 and 5 units of restriction enzyme Sal I was incubated at 37° C. for 1 hour in 50 μl of Sal I reaction mixture. DNA was recovered from the mixture and suspended in 20 μl of distilled water. To this DNA solution was added 2 units of Klenow-fragment of *E. coli* DNA Polymerase I and the mixture was incubated at 37° C. for 1 hour in 50 μl of polymerase reaction mixture [40 mM KPO$_4$ (pH 7.5), 6.6 mM MgCl$_2$, 1.0 mM 2-mercaptoethanol, 33μM dNTP].

Thereafter, DNA was recovered from the reaction mixture and suspended in 20 μl of distilled water. To 20 μl of this DNA solution were added about 1 μg of Hind III linker and 3 units of T$_4$ DNA ligase and the mixture was incubated at 16° C. for 3 hours in 60 μl of T4 DNA ligase reaction mixture.

*E. coli* DH1 was transformed with the reaction mixture and plasmid DNA was recovered from the resulted colonies.

The plasmid DNA (1 μg) obtained as above and 1 unit of restriction enzyme Hind III were incubated at 37° C. for 1 hour in 50 μl of Hind III reaction mixture. Thereafter, the resulting plasmids were analyzed by 0.8% agarose gel electrophoresis to select a plasmid which contained an about 1.8 Kb of Hind III fragment. The plasmid thus selected was named as pTF2.

Isolation of the Hind III fragment containing the P-450MC coding region

A mixture of 2 μg of pTF2 DNA and 2 units of restriction enzyme Hind III was incubated at 37° C. for 2 hours in 50 μl of Hind III reaction mixture, After DNA was recovered from the reaction mixture, it was subjected to 0.8% low melting point agarose gel electrophoresis and the gel band corresponding to 1.8 Kb of Hind III fragment was cut out, from which DNA was recovered. It was suspended in 20 μl of distilled water.

Construction of an expression plasmid

An expression plasmid pAMC1 was constructed by inserting the Hind III fragment containing the P-450MC coding region into the yeast expression vector plasmid pAAH5 with the ADH promotor [described in abandoned U.S. Ser. No. 299,733 to Washington Research Foundation available from Washington Research Foundation; prepared by the method of Ammerer et al., Methods in Enzymology, 101, part C, p 192-201] as follows:

(a): A mixture of 0.5 μg of the expression vector plasmid pAAH 5 with the ADH promotor and 1 unit of restriction enzyme Hind III was incubated at 37° C. for 1 hour in 50 μl of Hind III reaction mixture. DNA was recovered from the reaction mixture and suspended in 20 μl of distilled water. To this 20 μl of the DNA solution was added 2 units of alkaline phosphatase and the mixture was incubated at 60° C. for 1 hour in 100 μl of an alkaline phosphatase reaction mixture. DNA was recovered from the reaction mixture by twice of phenol extractions and precipitation with ethanol and suspended in 20 μl of distilled water.

(b): With 20 μl of solution of the Hind III fragment containing the P-450MC coding region prepared as above was combined 20 μl of the DNA solution prepared as above procedures (a), and 2 units of $T_4$ DNA ligase was added to the mixture, which was then incubated at 16° C. for 3 hours in a $T_4$ DNA ligase reaction mixture. After the reaction was over, E. coli DH1 was transformed with the reaction mixture and DNA was prepared from the resulted colonies. A mixture of 1 μl of the plasmid DNA and 1 unit of restriction enzyme Hind III was incubated at 37° C. for 1 hour in 50 μl of a Hind III reaction mixture and the plasmids were analyzed by 0.8% agarose gel electrophoresis to provide plasmids containing ca. 1.8 Kb of DNA fragment. Some of thus obtained plasmids contain the DNA fragment where the Hind III fragment of 1.8 Kb was linked to the ADH promor in two possible orientations.

Accordingly, 1 μg of thus selected plasmid DNA was mixed with 1 unit of restriction enzyme Stu I and 1 unit of restriction enzyme Bam H1 and incubated at 37° C. for 1 hour in 50 μl of Bam H1 reaction mixture. After the reaction was over, the reaction mixture was subjected to 0.8% agarose gel electrophoresis analysis to select plasmids from which 2.7 Kb and 1.1 Kb of DNA fragments were detected in addition to the DNA fragments derived from the expression vector plasmid pAAH5.

Thus selected plasmid contains the P-450MC gene connected to the ADH promotor in the correct orientation. It was named as pAHC1.

Transformation of yeast with the plasmid pAMC1

(a): S. cerevisiae strain AH22 was inoculated in 5 ml of YPAD-broth [1% yeast extract, 2% polypeptone, 2% glucose, 0.04% adenine] with a loop and the broth was shaken at 30° C. for 16-18 hours. Thereafter, cells were collected by centrifugation (5000×g, 5 minutes) and suspended in 5 ml of sterile water. By further centrifugation (5000×g, 5 minutes), pellets were obtained, which was then suspended in 2 ml of DTT solution [1.2M sorbitol, 25 mM EDTA, 50 mM DTT (pH 8.0)]. The suspension was allowed to stand at 30° C. for 10 minutes followed by centrifugation (3000×g, 2 minutes). Thus obtained pellets were resuspended in 5 ml of 1.2M sorbitol and centrifugated. The same centrifugation was repeated twice and the resulting pellets were suspended in 2 ml of a Zymolyase solution [1.2M sorbitol, 0.1M sodium succinate (pH 5.8), 0.2 mg/ml Zymolyase 60,000], which was then shaken at 30° C. for 1 hour. Pellets were obtained by centrifugation (3000×g, 2 minutes) of the mixture and resuspended in 5 ml of 1.2M sorbitol/10 mM $CaCl_2$ solution, which was then centrifuged [3000×g, 2 minutes]. The same centrifugation was repeated twice more and the resulting pellets were suspended in 0.5 ml of 1.2M sorbitol/10 mM $CaCl_2$ solution. To this solution was added approximately 1 μg of the plasmid pAMC1 and the mixture was allowed to stand at room temperature for 10 minutes. Then, 2 ml of a polyethylene glycol solution [20% polyethylene glycol 4000, 10 mM $CaCl_2$, 10 mM Tris-HCl (pH 7.5)] was added to the mixture, which was stirred and then allowed to stand at room temperature for 15 minutes. By centrifugation (3000×g, 2 minutes) were obtained pellets, to which 0.1 ml of 1.2M sorbitol/10 mM $CaCl_2$ solution and 0.05 ml of 1.2M sorbitol/YPAD broth were added.

The mixture was then shaken at 30° C. for 30 minutes and added to a regeneration medium (22% sorbitol, 2% glucose, 0.7% nitrogen base (w/o), 3% agar) warmed to 45° C.

The medium was then spread onto agar plates [22% sorbitol, 2% glucose, 0.7% nitrogen base (w/o), 2% agar, 20 μg/ml histidine) and incubated at 30° C. for 3-4 days to give a pure culture of transformant S. cerevisiae strain AH22 (pAMC1), which was deposited at Fermentation Research Institute, Japan, under the deposition No. 7752.

(b): With the same procedures as those of the above (a), S. cerevisiae strain SHY3 was transformed with the plasmid pAMC1 to give a pure culture of transformant S. cerevisiae strain SHY3 (pAMC1) containing the P-450MC gene, which was deposited at Fermentation Research Institute, Japan, under the deposition No. 7751.

In this transformation, agar plates containing 20 μg/ml of histidine, tryptophan, uracil and adenine were used.

(c): With the same procedures as those of the above (a), S. cerevisiae strain NA87-11A was transformed with the plasmid pAMC1 to give a colony of transformant S. cerevisiae strain NA87-11A (pAMC1) containing the P-450MC gene, which was deposited at Fermentation Research Institute, Japan, under the deposition No. 7753.

In this transformation, agar plates containing 20 μg/ml of histidine and tryptophan were used.

While, with the same procedures as those of the above (a)-(c) except that the expression vector pAAH5 was used instead of the plasmid pAMC1, transformant S. cerevisiae AH22 (pAAH5), SHY3 (pAAH5) and NA87-11A (pAAH5) were obtained.

Thus obtained transformant yeasts, S. cerevisiae strains SHY3 (pAMC1), AH22 (pAMC1) and NA87-11A (pAMC1) are novel strains and deposited at Fermentation Research Institute, Japan, according to the BUDAPEST TREATY under the deposition Nos. FERM BP-779, FERM BP-780 and FERM BP-781, respectively.

Expression of the rat liver cytochrome P-450MC in yeasts with the plasmid pAMC1

Expression of P-450MC in yeasts by the plasmid pAMC1 was confirmed, of which detail report is given below

Growth of the transformant yeasts and extraction

The transformant yeast, S. cerevisiae strain SHY3 (pAMC1) was grown in 10 ml of SD-synthetic broth [0.67% Bacto-yeast nitrogen base w/o amino acids (Difco), 2% dextrose, 20 mg/ml tryptophan, 20 μg/ml histidine, 20 μg/ml adenine sulfate] from which leucine was excluded, to a density of $2 \times 10^7$ cells/ml. Cells were collected by centrifugation of 1 ml of the culture medium at 7,000 rpm for 3 minutes and suspended in 1 ml of 1.2M sorbitol. After further centrifugation, cells were resuspended in 0.2 ml of Zymolyase solution [1.2M sorbitol, 50 mM potassium phosphate (pH 7.5), 14 mM 2-mercaptoethanol, 400 μg/ml Zymolyase 60,000] and incubated at 30° C. for 30 minutes. By centrifugation at 7,000 rpm for 3 minutes, spheroplasts were collected and washed with 0.4 ml of buffer A [1.2M sorbitol, 50 mM Tris-HCl (pH 7.5)]. They were centrifuged again and resuspended in 50 μl of SDS solution [2% sodium dodecylsulfate, 50 mM Tris-HCl (pH 7.5). The mixture was heated at 100° C. for 5 minutes and centrifuged at 10,000 rpm for 5 minutes. The supernatant was combined with 50 μl of sample buffer [62.5 mM Tris-HCl (pH 6.8), 2% (w/v) sodium dodecylsulfate, 5% (v/v) 2-mercaptoethanol, 10% (w/v) glycerol, 0.001% bromophenol blue].

Determination of the protein synthesized in yeast

Of approximately 100 μl of the crude extract of the S. cerevisiae strain SHY3 (pAMC1) obtained as above, 20 μl was electrophoresed on SDS-polyacrylamide gel according to the method of Laemmali et al., [Nature, 227, 680–685 (1970)]. After the electrophoresis, a nitrocellulose filter (Schleicher & Senüll) was attached to the polyacrylamide gel and protein was electrophoretically transferred to the nitrocellulose filter at 30 volts for about 10 hours in a blotting buffer [25 mM Tris-HCl (pH 8.3), 192 mM glycine, 20% methanol]. Thereafter, the nitrocellulose filter was immersed in a blocking solution [3% gelatin, 50 mM Tris-HCl (pH 7.5), 200 mM NaCl, 0.05% Tween 20] and stirrered for 30 minutes. It was then immersed in a buffer [1% gelatin, 50 mM Tris-HCl (pH 7.5), 200 mM NaCl, 0.05% Tween 20] containing 1 μg/ml of anti-P-450MC IgG and stirred for further 2 hours. Then, the nitrocellulose filter was washed 4 times with TBS-solution [50 mM Tris-HCl (pH 7.5), 200 mM NaCl] containing 0.05% Tween 20 for 40 minutes and immersed again in a blocking solution. After the blocking solution was removed, it was immersed in 50 ml of $^{125}$I-Protein A solution (7 μCi) for 1 hour and washed 4 times with TBS-solution containing 0.05% Tween 20 for 30 minutes. Finally, it was washed with TBS-solution. Thus treated nitrocellulose filter was dried on filter papers and autoradiographed.

FIG. 5 shows the results of the analysis of the proteins synthesized in the transformant S. cerevisiae strains SHY3 (pAMC1) and SHY3 (pAAH5).

A is the result of the analysis of the protein synthesized in the control strain, S. cerevisiae SHY3 (pAAH5), wherein no protein which was recognized by the anti-P-450MC IgG was detected.

While, B is the result of the analysis of the protein synthesized in the transformant yeast carrying the expression plasmid pAMCI, wherein the protein which reacted with the anti-P-450MC IgG was detected at the position corresponding to the molecular weight of P-450MC.

It became apparent from the comparison with known amounts of the authentic P-450MC that approximately $4 \times 10^5$ molecules per cell of P-450MC was produced.

Expression of P-450MC was also confirmed with the transformants, S. cerevisiae strains AH22 (pAMC1), and NA87-11A (pAMC1).

The transformant yeasts obtained as above were grown to a density of $2 \times 10^7$ cells/ml under the same growing conditions as above. The culture medium (100 ml) of each of the transformants was centrifuged ($6000 \times g$, 10 minutes) to harvest the transformant cells, which were then suspended in 50 ml of distilled water and recentrifuged at $6000 \times g$ for 10 minutes. After the cells were resuspended in 10 mM potassium phosphate buffer (pH 7.4) to a density of ca. $10^9$ cells/ml, the reduced CO-difference spectrum was measured according to the method [J. Biol. Chem. 289, 2870 (1964)].

Figure 6B:
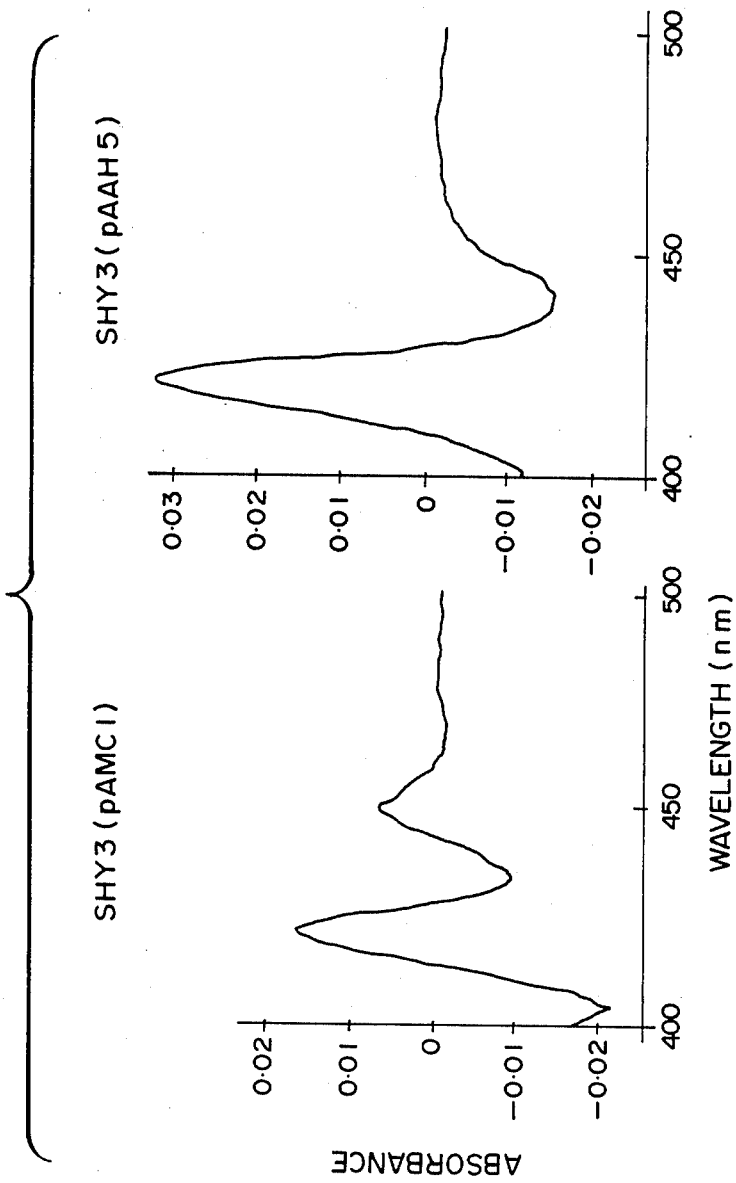
FIGS. 6 (a)–(c) show the reduced CO-difference spectra of the transformant yeasts provided by the present invention, S. cerevisiae strains AH22 (pAMC1), SHY3 (pAMC1) and NA87-11A (pAMC1) and the yeasts transformed with the plasmid pAAH5 which contains no P-450MC gene.
Figure 7:
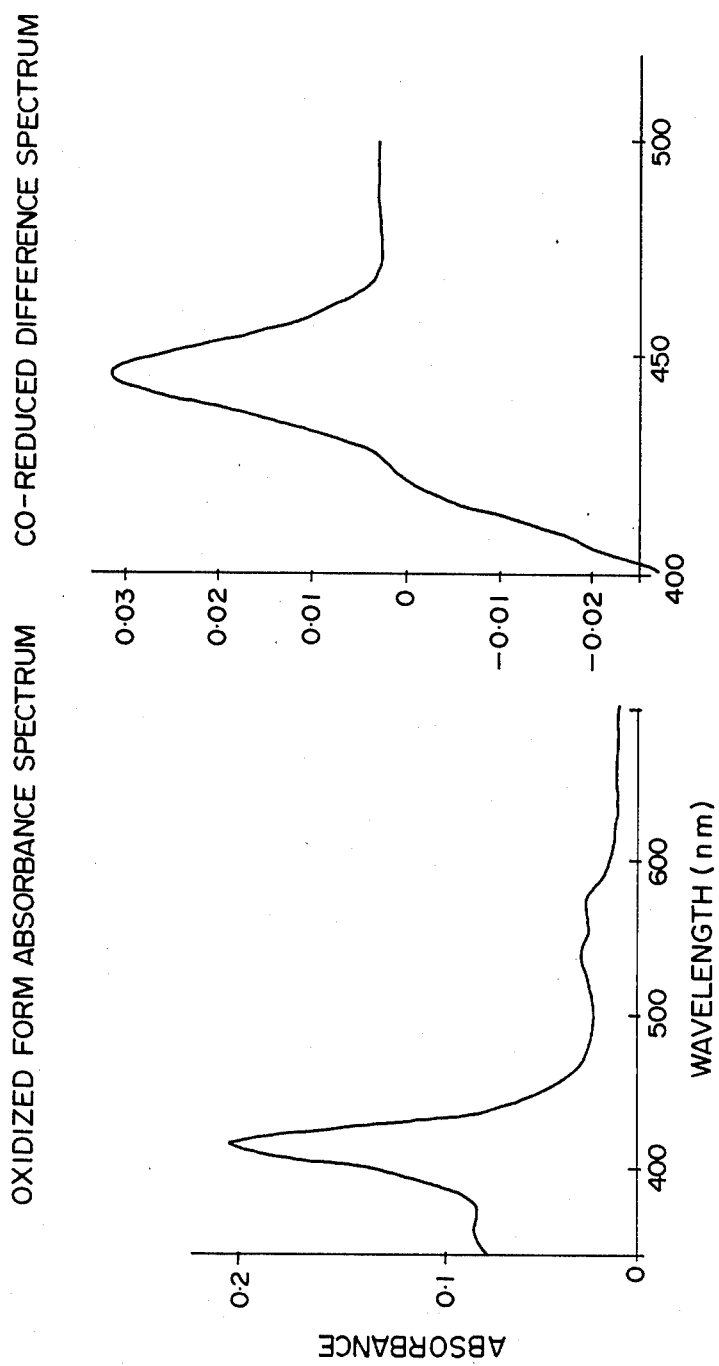
FIG. 7 shows the oxidized and CO-reduced difference spectra of the purified P-450MC. The oxidized spectrum is a typical low spin spectrum and shows a peak at 417 nm. The CO-reduced difference spectrum has a peak at 447 nm.

The results are given in FIG. 6. As is clear from the FIG. 6, there is no peak at 450 nm in the spectra of the yeasts carrying the plasmids pAAH5 with no P-450MC coding region, i.e., S. cerevisiae strains AH22 (pAAH5), SHY3 (pAAH5), and NA87-11A (pAAH5). While, the spectra of S. cerevisiae strains AH22 (pAMC1), SHY3 (pAMC1) and NA87-11A (pAMC1), which contain the plasmid pAMC1 with the P-450MC coding region have a peak at about 450 nm attributable to P-450MC.

By analyzing the data taking into the consideration the fact that, when measured with cells, obtained values are lower (about ⅔) than the actual amount of P-450MC, it was found that the S. cerevisiae strain AH22 (pAMC1) produced $4 \times 10^5$ molecules/cell of P-450MC hemoprotein and that both the S. cerevisiae strains SHY3 (pAMC1) and NA87-11A (pAMC1) produced about $1.5 \times 10^5$ molecules/cell of P-450MC hemoprotein. This means that about 50% of the P-450MC synthesized in S. cerevisiae AH22 (pAMC1) contained heme in their molecule and about 40% of P-450MC synthesized in the S. cerevisiae SHY3 (pAMC1) and NA87-11A (pAMC1) contain heme.

Isolation of the microsomal fraction

S. cerevisiae strain AH22 (pAMC1) was grown to $2.0 \times 10^7$ cells/ml and the cells were harvested from 3.3 l of the culture broth.

The cells were suspended in 100 ml of buffer A (10 mM Tris-HCl (pH 7.5), 2M sorbitol, 0.1 mM DTT, 0.2 mM EDTA) and 300 mg of Zymolyase 5000 was added to the suspension, which was then incubated at 30° C. for 60 minutes. The spheroplasts were collected by centrifugation at $5000 \times g$ for 10 minutes. They were suspended in 100 ml of the buffer A and recentrifuged ($5000 \times g$, 10 minutes). The centrifugation was repeated one more time to wash the spheroplasts, which was then suspended in 60 ml of buffer [10 mM Tris-HCl (pH 7.5), 0.65M sorbitol, 0.1 mM DTT] and destructed by sonication. Thereafter, the mixture was centrifuged at $10000 \times g$ for 20 minutes and the supernatant was recentrifuged at $125000 \times g$ for 70 minutes. The precipitates were suspended in a buffer [0.1M potassium phosphate (pH 7.2), 10 mM EDTA] and then homogenized. The homogenized mixture was again centrifuged at 125000×g for 70 minutes. Thus obtained precipitates were suspended in 11 ml of a potassium phosphate buffer (pH 7.4) and homogenized to give the microsomal fraction.

The oxidizing activity of the microsomal fraction was measured as follows:

Determination of benzo(a)pyrene-hydroxylase activity

After 86 μl of the microsomal fraction obtained as above (containing 0.3 n mol of P-450MC), 1.0 ml of 0.1M potassium phosphate buffer (pH 7.0) and 25 μl of 20 mM NADPH aqueous solution were combined and shaken at 37° C. for 3 minutes, 30 μl of 4 mM benzo(a)pyrene in acetone was added to the mixture to start the reaction. After the mixture was incubated at 37° C. for 2, 5 or 10 minutes, 1.0 ml of chilled acetone water was added to stop the reaction. Thereafter the reaction mixture was again centrifuged at 2000×g for 5 minutes to give 0.6 ml of supernatant. To this supernatant was added 1.4 ml of 8.5% triethyl amine aqueous solution and 3-hydroxybenzo(a)pyrene, the reaction product was measured. The result indicated that the reaction rate was 0.87 n mol of 3-hydroxybenzo(a)pyrene/min/nmol P-450MC.

This activity was specifically inhibited by anti-P-450MC IgG prepared from rabbit antiserum. This indicates that the benzo(a)pyrene-hydroxylase activity is dependent upon P-450MC. No activity was detected with the microsomal fractions obtained from S. cerevisiae strain AH22 (pAAH5) tested as a control.

Determination of the activity to O-deethylation of 7-ethoxycoumarin

A mixture of the microsomal fraction of the S. cerevisiae strain AH22 (pAMC1) obtained as above (86 μl, containing 0.3 nmol of P-450MC), 1.0 ml of 0.1M potassium phosphate buffer (pH 7.0) and 25 μl of 20 mM NADPH aqueous solution was shaken at 37° C. for 3 minutes, to which 25 μl of 20 mM 7-ethoxycoumarin [dissolved in a mixture of methanol and water (1:1)] was added to start the reaction. After the mixture was incubated at 37° C. for 2, 5 or 10 minutes, the reaction was stopped by addition of 62.5 μl of 15% trichloroacetic acid aqueous solution. Measurement of the reaction product, 7-hydroxycoumarin was performed according to the method of J. Pharmacol. Exp. Ther., 205, 596 (1978). The reaction rate was 1.1 nmol 7-hydroxycoumarin/min/nmol P-450MC.

No O-deethylation activity was detected with the microsomal fractions derived from the strain AH22 (pAAH5) used as a control.

The followings are examples of isolation and purification of P-450MC:

Step 1: Solubilization of microsomes

To 15 ml of the microsomal fraction of S. cerevisiae strain AH22 (pAMC1) prepared as above (82 nmol P-450MC/205 mg protein) was added buffer B [10 mM potassium phosphate (pH 7.4), 20% glycerol, 0.5% cholic acid, 0.2% Emulgen 913, 0.1 mM EDTA]. After the mixture was stirred at 4° C. for 10 minutes, it was centrifuged at 125000×g for 70 minutes. The supernatant was then dialyzed for 14 hours against 5 l of a dialysis buffer [20 mM potassium phosphate (pH 7.4), 20% glycerol, 0.2% Emulgen 913].

Step 2: DEAE-cellulose column chromatography (First)

The solubilized microsomes dialyzed as above were applied to a DEAE-cellulose column (1.6×15 cm) equilibrated with buffer B and washed with 40 ml of buffer B. The red band at the upper part of the column was cut out.

Step 3: DEAE-cellulose column chromatography (Second)

The gel obtained in Step 2 above was suspended in buffer B and then applied to a new column (1.6×20 cm) and eluted with 150 ml of buffer B with KCl linear gradient from 20 to 200 mM. The obtained P-450MC eluate was dialyzed for 14 hours against 2 l of a dialysis buffer [20 mM potassium phosphate (pH 7.4), 20% glycerol, 0.2% Emulgen 913].

Step 4: Hydroxylapatite column chromatography

The solution containing P-450MC prepared in Step 3 above was applied to a hydroxylapatite column (1.6×7 cm) equilibrated with 10 mM potassium phosphate (pH 7.4) and eluted with 120 ml of buffer B with potassium phosphate linear gradient from 10 to 250 mM. The obtained eluate containing P-450MC was dialyzed against 2 l of a dialysis buffer [20 mM potassium phosphate (pH 7.4), 20% glycerol, 0.2% Emulgen].

Step 5: DEAE-Sepharose CL-6B column chromatography

The P-450MC solution obtained in Step 4 above was applied to a DEAE-Sepharose CL-6B (0.9×5 cm) equilibrated with 33 mM potassium phosphate buffer (pH 7.4) containing 20% glycerol and washed with the same equilibration buffer.

When $A_{280}$ reached to 0.005, the column was eluted with the equilibration buffer containing 400 mM KCl. The content of P-450MC in thus obtained product was 14 nmol/mg protein.

We claim:

1. An expression vector plasmic for *Saccharomyces cerevisiae* which comprises rat liver cytochrome P-450MC gene inserted into an expression vector plasmid with the yeast alcohol dehydrogenase promoter I and terminator and which expresses the rat liver cytochrome P-450MC.

2. The expression vector plasmid as in claim 1 which comprises plasmid pAMC1.

3. Transformed *Saccharomyces cerevisiae* which are transformed with expression vector plasmids which comprise the rat liver cytochrome P-450MC gene inserted into an expression vector plasmid with yeast alcohol dehydrogenase promoter I and terminator, and which produce rat liver cytochrome P-450MC in their cells.

4. The transformed *Saccharomyces cerevisiae* according to claim 3 which are transformed with the expression vector plasmid pAMC1.

5. The transformed *Saccharomyces cerevisiae* according to claim 3 which are *S. cerevisiae* strain AH22-(pAMC1) (FERM-BP780).

6. The transformed *Saccharomyces cerevisiae* according to claim 3 which are *S. cerevisiae* strain SHY3(-pAMC1) FERM-BP779.

7. The transformed *Saccharomyces cerevisiae* according to claim 3 which are *S.cerevisiae* strain NA87-11A(-pAMC1) (FERM-BP781).

8. A process for producing rat liver cytochrome P-450MC which comprises culturing transformed *Saccharomyces cerevisiae* which transformed with expression vector plasmids comprising rat liver cytochrome P-450MC gene inserted into an expression vector plasmid with yeast alcohol dehydrogenase promoter I and terminator in a suitable medium.

* * * * *